United States Patent [19]
Reichert et al.

[11] Patent Number: 6,153,813
[45] Date of Patent: Nov. 28, 2000

[54] **METHODS FOR GENOTYPE-INDEPENDENT NUCLEAR AND PLASTID TRANSFORMATION COUPLED WITH CLONAL REGENERATION UTILIZING MATURE ZYGOTIC EMBRYOS IN RICE (*ORYZA SATIVA*) SEEDS**

[75] Inventors: Nancy A. Reichert; Vanishree Rudraswamy, both of Mississippi State; Liza Ming-Ju Chen, Starkville, all of Miss.

[73] Assignee: Mississippi State University, Mississippi State, Miss.

[21] Appl. No.: 09/209,466

[22] Filed: Dec. 11, 1998

Related U.S. Application Data

[60] Provisional application No. 60/069,678, Dec. 11, 1997.

[51] Int. Cl.[7] ............................. A07H 1/00; C12N 15/29; C12N 15/82; C12N 15/00; A01H 1/06
[52] U.S. Cl. ......................... 800/293; 800/293; 800/278; 800/320.2; 435/440; 435/468; 435/470
[58] Field of Search ...................................... 800/293, 278, 800/320.2; 435/440, 468, 470

[56] References Cited

U.S. PATENT DOCUMENTS 5,141,131  8/1992  Miller, Jr. et al. ...................... 222/54

OTHER PUBLICATIONS

Cao et al., Transformation of Rice and Maize Using the Biolistic Process UCLA Symposia on Molecular and Cellular Biology, vol. 129, pp 21–33, 1990.

Christou et al., Production of Transgenic Rice (*Oryza Sativa*) Plants from Agronomically Important Indica and Japonica Varieties via Electric Discharge Particle Acceleration of Exogenous DNA into Immature Zygotic Embryos, Bio/Technology, vol. 9, pp. 957–, 1991.

Riazuddin et al., Insect Resistant Transgenic Basmati Rice, Rice Biotechnology Quarterly, vol. 23, pp 7–8, 1995.

*Primary Examiner*—David T. Fox
*Assistant Examiner*—Anne Marie Grünberg
*Attorney, Agent, or Firm*—Long, Aldridge & Norman, LLP; Steven B. Kelber

[57] ABSTRACT

A method for transforming rice plants to express heterologous DNA which involves the biolistic bombardment of mature rice seeds (embryo bearing) and results in expression of the heterologous DNA coated on the biolistic particle in the post-bombardment embryo. The heterologous DNA may be introduced as a plastid, as opposed to bare DNA. The transformed rice embryo is regenerated into a rice plantlet which can be transferred from greenhouse to field.

2 Claims, No Drawings

METHODS FOR GENOTYPE-INDEPENDENT NUCLEAR AND PLASTID TRANSFORMATION COUPLED WITH CLONAL REGENERATION UTILIZING MATURE ZYGOTIC EMBRYOS IN RICE (*ORYZA SATIVA*) SEEDS

This application is a regular National application claiming priority from Provisional Application, U.S. Application Ser. No. 60/069,678 filed Dec. 11, 1997. The entire disclosure of the priority application is incorporated herein by reference.

BACKGROUND OF THE INVENTION

Field of the Invention

This invention relates to 1) a process of rice plant regeneration from mature zygotic embryos excised from mature rice seeds 2) two processes of transformation (nuclear and plastid) utilizing rice seeds with embryos via biolistics-based particle bombardment and 3) use of the above processes to produce transgenic (nuclear-transformed) and transplastomic (plastid-transformed) rice plants 4) production of transgenic and transplastomic plants carrying novel phenotypes (e.g. herbicide resistance).

SUMMARY OF THE INVENTION

In general, rice regeneration protocols coupled with nuclear transformation utilize either immature zygotic embryos (12–15 days post-pollination; dpp) or callus generated from them, or mature embryo-derived callus and suspension cells. Disadvantages include the stringency in age requirement—panicles have to be manually pollinated, dated, and harvested at specific dpp. The availability of materials is fairly season-dependent, and once harvested, they retain viability for a short time period. The extraction of the embryos is extremely laborious. Transgenic rice production to date utilizes Accell™ technology (commercially unavailable but genotype-independent) and particle bombardment.

Currently, all rice regeneration protocols coupled with nuclear transformation protocols are callus-based. Callus-base regeneration systems have been determined to contribute undesirable genetic variation in the regenerated plants and their progeny. Direct multiple shoot induction from the embryos excised from seeds are not associated with variation and has proven to be faster.

There is no report available to date for production of transplastomic (plastid-transformed) plants particularly in economically important crops. Transplastomic technology in higher plants dawned with the creation of transplastomic tobacco and is still in its infancy. Transient expression of β-glucuronidase (GUS) has been noted in cultured tissues of Arabidopsis, and in lower land plants like liverwort and hornwort. In those cases, transformation was achieved via PEG-mediated DNA transfer into protoplasts and particle bombardment.

Our protocols exclusively utilize mature rice seeds for transformation. There are no reports available regarding the direct use of mature rice seeds as targets for gene delivery. In addition, a rice multiple shoot induction protocol has not been coupled to any transformation protocol. We have proven that mature seeds (embryos excised two days post-bombardment) make ideal targets in genotype-independent biolistics-based nuclear and plastid transformation protocols to yield genetically altered rice plantlets.

DETAILED DESCRIPTION OF THE INVENTION

Surface-disinfested seeds (de-hulled) are pre-cultured for 3–4 days in liquid MS media containing a cytokinin, 6-benzylaminopurine (BAP: 2 mg/l), then the germinating embryo portion is separated and placed in liquid MS media containing higher concentrations of a cytokinin (BAP: 2–8 mg/l). Multiple shoots were initiated from the germinating embryo within 8 weeks of culture under continuous light conditions. Shoots are separated and rooted within one week in liquid MS media containing indole-3-butyric acid (IBA: 0.5 mg/l). Plantlets are acclimatized and transferred to the greenhouse.

Mature seeds pre-cultured overnight are placed vertically (25 per plate, embryo end up) and tightly packed in a 2.5 cm diameter circle at the center of a plate containing semisolid pre-culture media just prior to bombardment with the PDS-1000/He apparatus (Bio-Rad; only commercially available gene gun). The embryo side of the seeds are bombarded twice with DNA-coated tungsten microprojectiles [size: 1.63 $\mu$m (nuclear) and 0.36 $\mu$m (plastid)] using 650 psi helium pressure, 1.0 cm gap and 7.5 cm target distance. Two days post-bombardment, embryos were excised from seeds and placed in culture media containing a selective agent (glufosinate herbicide Ignite; 0.25 mg/l). Transient nuclear expression of the β-glucuronidase (GUS) gene (part of introduced foreign DNA; plasmid pAHC25; nuclear transformation vector) could be detected three days post-bombardment. Results indicated that bombarded embryos could yield "complete" transformants (all cells received introduced DNA in their nuclei; whole embryos turned blue after histochemical GUS assay). Details of biolistic bombardment of other plant species, including soybeans, can be found in U.S. patent application Ser. No. 08/825,469, allowed now U.S. Pat. No. 5,968,830, incorporated hereinby-reference.

For plastid transformation, the seeds are bombarded as previously stated with a plastid transformation vector (contains aadA gene for selection—confers resistance to antibiotics spectinomycin and streptomycin sulfate; vector provided by Dr. Henry Daniell—Auburn University) and selected in liquid culture media containing spectinomycin (500 mg/l) and streptomycin sulfate (100 mg/l). This has proven successful with six genotypes tested to date, again indicating genotype-independence. At least two transplastomic 'Priscilla' rice plants have been regenerated to date—confirmed by polymerase chain reaction (PCR) using plastid DNA-specific primer. These are the two first rice transplastomic plants ever generated.

Development of faster nuclear and plastid transformation protocols for rice is of great interest and value to researchers in both private and public sectors world-wide. Transplastomic herbicide resistant rice created via this technology is the best solution for eradication of red rice in rice producers' fields. This technology precludes undesired gene transfer via pollen to red rice weeds (because plastids are maternally inherited and pollen contamination will not lead to creation of herbicide resistant weeds). This technology could also serve as a model to unravel regulated gene expression in monocot plastids.

More importantly, introduction of a gene into the plastid genome of plants should ensure high levels of expression of the gene product. This is due to there being numerous copies of the gene in each plastid and that there are numerous plastids per plant cell. This monocot model system therefore would have numerous applications in areas where plants are to be used as "factories" to produce the desired proteins/products.

What is claimed is:

1. A method for transforming rice plants to express heterologous DNA, comprising:

culturing a mature rice plant seed until a transformable rice plant embryo is formed in said mature seed, bombarding said mature seed comprising said embryo with biolistic projectiles bearing said heterologous DNA, excising said embryo after bombardment of said mature seed, and culturing said excised embryo to form a rice plant expressing said heterologous DNA.

2. The method of claim 1, wherein said heterologous DNA is in the form of a transformation vector.

* * * * *